(12) United States Patent
Kellner et al.

(10) Patent No.: US 10,471,247 B2
(45) Date of Patent: Nov. 12, 2019

(54) CATHETER COUPLING

(71) Applicants: Raumedic AG, Münchberg (DE); B. Braun Melsungen AG, Melsungen (DE)

(72) Inventors: Thorsten Kellner, Bayreuth (DE); Frank Skaper, Leupolsfrün (DE); Thomas Jakob, Rehau (DE); Manuela Bezela, Morschen (DE); Iris Blum, Fruldabrück (DE); Martin Sippel, Melsungen (DE); Heinz Wiegel, Alheim (DE)

(73) Assignees: Raumedic AG, Münchberg (DE); B. Braun Melsungen AG, Melsungen (DE)

( * ) Notice: Subject to any disclaimer, the term of this patent is extended or adjusted under 35 U.S.C. 154(b) by 978 days.

(21) Appl. No.: 14/420,758

(22) PCT Filed: Aug. 2, 2013

(86) PCT No.: PCT/EP2013/066277
§ 371 (c)(1),
(2) Date: Feb. 10, 2015

(87) PCT Pub. No.: WO2014/026864
PCT Pub. Date: Feb. 20, 2014

(65) Prior Publication Data
US 2015/0217105 A1    Aug. 6, 2015

(30) Foreign Application Priority Data
Aug. 17, 2012 (DE) .................. 20 2012 007 845 U

(51) Int. Cl.
*A61M 39/10* (2006.01)
*A61M 39/12* (2006.01)

(52) U.S. Cl.
CPC ........ *A61M 39/1011* (2013.01); *A61M 39/10* (2013.01); *A61M 39/12* (2013.01)

(58) Field of Classification Search
CPC .............. A61M 25/0014; A61M 39/10; A61M 39/1011; A61M 39/12; A61M 5/1418;
(Continued)

(56) References Cited

U.S. PATENT DOCUMENTS 3,785,683 A    1/1974  Adelhed
4,950,255 A    8/1990  Brown et al.
(Continued)

FOREIGN PATENT DOCUMENTS

CN    101618248    1/2010
DE    84 25 441.6   11/1984
(Continued)

OTHER PUBLICATIONS

Office Action dated Feb. 28, 2017 in RU App. No. 2014135288/14.
(Continued)

*Primary Examiner* — Bhisma Mehta
*Assistant Examiner* — Larry R. Wilson
(74) *Attorney, Agent, or Firm* — Boyle Fredrickson S.C.

(57) ABSTRACT

A catheter coupling has a tubing and two jaws extending in the longitudinal direction of the tubing which form a channel having an orifice to accommodate an end section of a catheter when the jaws abut against each other. The jaws are interconnected at a respective jaw end via a jaw joint having a joint axis extending transversely to the tubing. The other jaw end includes a snap-in locking member and a counter snap-in locking member, respectively, interacting therewith to form a snap-in locking arrangement. In the engagement position, the tubing is deformed by at least one jaw deformation component to securely accommodate the catheter. The coupling has at least one inspection window that allows
(Continued)

a stop in the tubing for the end section of the catheter to be visually inspected to prevent an end section of the catheter from being introduced into the tubing if it is too short.

17 Claims, 5 Drawing Sheets

(58) Field of Classification Search
CPC .............. A61M 25/0097; A61M 25/02; A61M 2039/1061; A61M 2025/024
See application file for complete search history.

(56) References Cited

U.S. PATENT DOCUMENTS

| | | | | |
|---|---|---|---|---|
| 6,350,260 | B1 * | 2/2002 | Goebel | ............. A61M 25/0014 |
| | | | | 604/533 |
| 6,506,181 | B2 | 1/2003 | Meng et al. | |
| 6,676,652 | B2 | 1/2004 | Mogg | |
| 8,142,417 | B2 | 3/2012 | Pajunk et al. | |
| 8,876,798 | B2 * | 11/2014 | Clark | ................. A61M 39/1011 |
| | | | | 604/533 |
| 2006/0129134 | A1 * | 6/2006 | Kerr | ................. A61M 25/0068 |
| | | | | 604/539 |

FOREIGN PATENT DOCUMENTS

| | | |
|---|---|---|
| DE | 90 15 688 | 3/1991 |
| DE | 601 20 293 | 6/2007 |
| DE | 10 2007 029 229 | 12/2008 |
| EP | 0 340 427 | 11/1989 |
| EP | 1 033 146 | 9/2000 |
| JP | 2000245850 | 9/2000 |

OTHER PUBLICATIONS

Office Action dated May 22, 2017 in CN App. No. 2013800148869.
Office Action dated Apr. 25, 2017 in JP App. No. 2015-526927.
First Office Action dated Jul. 1, 2016 in corresponding CN App. No. 2013800148869.
Second Office Action dated Jan. 4, 2017 in corresponding CN App. No. 2013800148869.
Search Report dated Jun. 20, 2016 in corresponding CN App. No. 2013800148869.
Ambulante Anasthesie (B. Braun Melsungen), p. 41, Jun. 2012.
Ambulante Anasthesie (B. Braun Melsungen) Jun. 2012.
B. Braun Regional Anesthesia: Customers' First Choice for Safe Pain Therapy Jun. 2012.

* cited by examiner

CATHETER COUPLING

CROSS-REFERENCE TO RELATED APPLICATIONS

This application claims the priority of German Utility Model Application No. 20 2012 007 845.3 filed on 17 Aug. 2012, pursuant to 35 U.S.C.: 119(a)-(d), the content of which is incorporated herein by reference in its entirety as if fully set forth herein.

FIELD OF THE INVENTION

The invention relates to a catheter coupling comprising a tubing and two jaws extending in a longitudinal direction of the tubing which, together with the tubing, form a channel having an orifice to accommodate an end section of a catheter when the jaws abut against each other, wherein the jaws are interconnected at a respective jaw end via a jaw joint having a joint axis extending transversely to the tubing, with the other jaw ends being in each case provided with a snap-in locking member and a counter snap-in locking member, respectively, interacting therewith, causing the two locking members to form a snap-in locking arrangement; wherein the tubing is deformed by at least one jaw deformation component to securely accommodate the catheter end section when the snap-in locking arrangement is in an engagement position.

BACKGROUND OF THE INVENTION

A catheter coupling of this type is known from EP 1 033 146 B 1.

SUMMARY OF THE INVENTION

An object of the present invention is to provide a catheter coupling which is less complicated to use.

The inspection window prevents an end section of the catheter from being accidentally inserted into the tubing if said end section is too short.

According to an additional aspect of the invention, a recess is arranged between the snap-in locking member adjacent to the orifice and a head section of the coupling in which the orifice is formed, which recess allows the head section to move relative to the snap-in locking member. Due to the fact that according to this additional aspect, the recess allows the head section to move relative to the snap-in locking member, a movement of the head section of the catheter coupling relative to the snap-in locking device is possible even if the jaws are pivoted relative to each other via the jaw joint. As a result, a deformation of the snap-in locking member caused by a pressure applied to the head section of the coupling is prevented. The snap-in locking device provides a predefined closing force even if such a pressure is exerted. This facilitates the use of the catheter coupling by preventing a faulty operation which might impair the snap-in locking device.

According to another aspect of the invention, one of the jaws forms part of the base body of the coupling which carries the tubing, wherein the base body jaw has protective webs between which the tubing is arranged in such a way as to be recessed therein. This aspect ensures that the catheter coupling is composed of a low number of independent components. When the jaw joint is folded out, the tubing is protected against an undesired deformation by the protective webs. The protective webs may be arranged on both sides of the tubing. The protective webs may be continuous; alternatively, the protective webs may be interrupted.

The above aspects may each be combined with the catheter coupling comprising a tubing and two jaws extending in a longitudinal direction of the tubing which, together with the tubing, form a channel having an orifice to accommodate an end section of a catheter when the jaws abut against each other, wherein the jaws are interconnected at a respective jaw end via a jaw joint having a joint axis extending transversely to the tubing, with the other jaw ends being in each case provided with a snap-in locking member and a counter snap-in locking member, respectively, interacting therewith, causing the two locking members to form a snap-in locking arrangement; wherein the tubing is deformed by at least one jaw deformation component to securely accommodate the catheter end section when the snap-in locking arrangement is in an engagement position, or they may be randomly combined with each other.

An arrangement in which one of the jaws is part of a base body of the coupling which carries the tubing proved to be practical. The number of independent components of the catheter coupling is small.

A two-component (2C) configuration in which the tubing is integrally connected to the base body jaw, wherein the tubing is configured as a soft component while the jaw is configured as a hard component of a 2C component proved to be particularly suitable. The soft tubing is easily deformable to securely accommodate the end section of the catheter.

In one embodiment, the base body jaw is provided with protective webs between which the tubing is arranged in such a way as to be recessed therein. The tubing is thus protected against an undesired deformation by means of the protective webs when the jaw joint is folded out. The protective webs may extend along the tubing. The protective webs may be arranged on both sides of the tubing. The protective webs may be continuous; alternatively, the protective webs may be interrupted.

The joint jaw that is articulated to the base body jaw may be provided with recesses which are engaged by the protective webs when the jaws abut against each other. These recesses may at least partly be configured in such a way as to be complementary to the protective webs. When interacting with the protective webs, the recesses may in this case also fulfil the function of guiding a pivoting movement of the jaws moving relative to each other.

A concave contact surface of at least one jaw deformation component which abuts against the outside of the tubing when the jaws abut against each other facilitates a defined deformation of the tubing by means of the at least one jaw deformation component, thus preventing an undesired yielding of the tubing. The concave curvature of the contact surface may extend about an axis which is parallel to the longitudinal axis of the tubing that is in contact therewith.

A design in which at least two jaw deformation components are provided which are spaced from each other along the tubing when the jaws abut against each other proved to be suitable and sufficient in order to securely accommodate the catheter end section. Alternatively, a jaw deformation component may be provided which continuously extends along at least a portion of the tubing.

Exemplary embodiments of the invention will be explained in more detail below with reference to the drawings.

DESCRIPTION OF THE PREFERRED EMBODIMENTS

Figure 1:
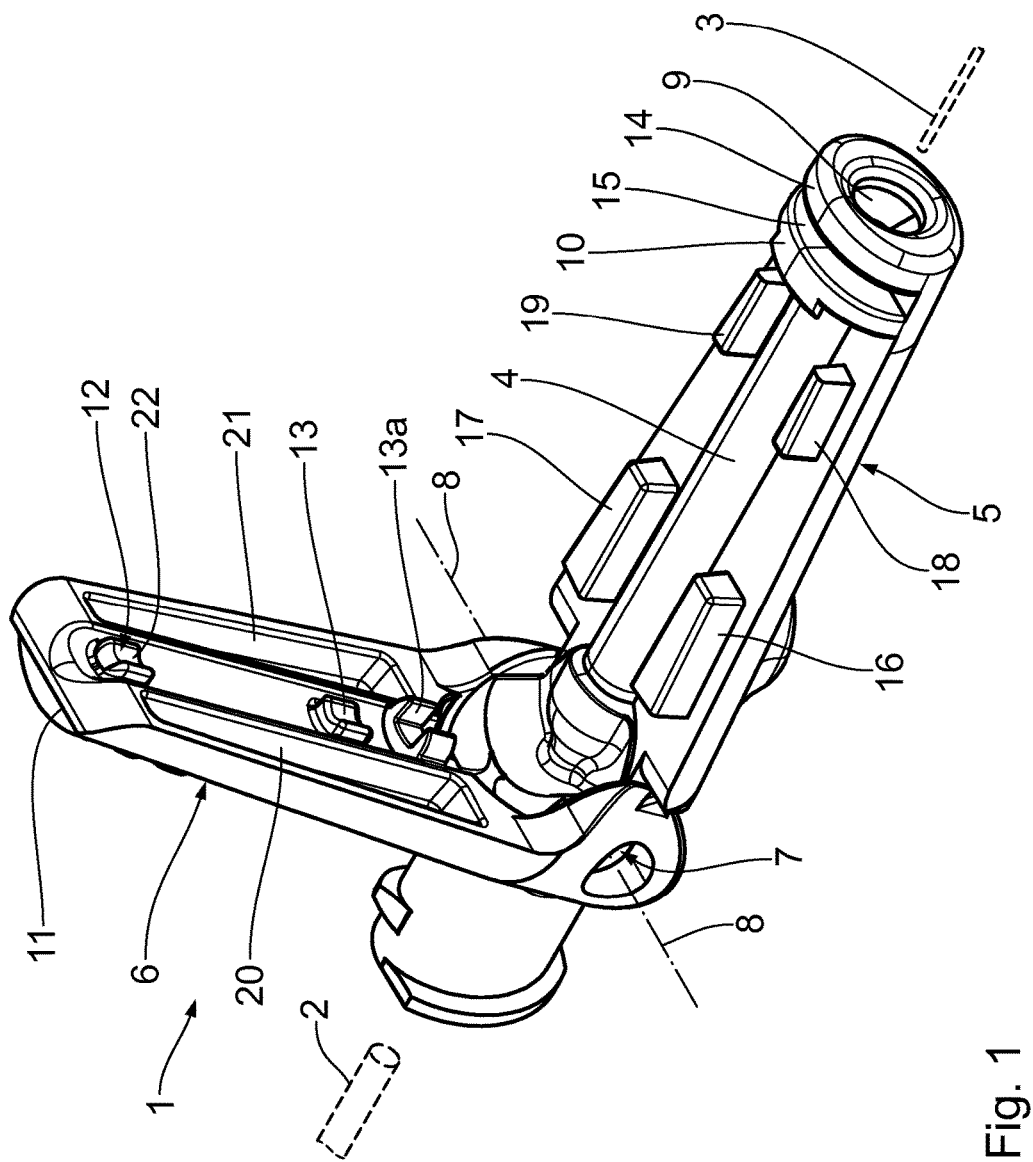
FIG. 1 shows a perspective view of a catheter coupling comprising a tubing and two jaws extending in the longitudinal direction of the tubing, wherein the jaws are shown in a folded-out position.

A catheter coupling 1 serves to provide a fluid communication between a tube 2, shown by dashed lines in FIG. 1, and a catheter 3 which is outlined by dashed lines in FIG. 1 as well.

The catheter coupling 1 has a coupling tubing 4 and two jaws extending in the longitudinal direction of the tubing, namely a base body jaw 5 and a joint jaw 6.

The base body jaw 5 is part of a base body of the catheter coupling 1 which carries the tubing 4.

The tubing 4 is integrally connected to the base body jaw 5. The base body was manufactured by 2C injection molding, with the tubing 4 being configured as a soft component while the base body jaw 5 is configured as a hard component.

The two jaws 5, 6 are interconnected via a jaw joint 7 having a joint axis 8 extending transversely to a longitudinal extension of the tubing 4. In a folded-in position not shown in the drawing, in other words in a condition where they abut against each other along the tubing 4, the jaws 5, 6 form a channel together with the tubing 4 which channel has an orifice 9 so as to accommodate an end section of the catheter 3.

The respective ends of the two jaws 5, 6 facing away from the joint 7 are in each case provided with a locking member 10, 11. The snap-in locking member 10 of the base body jaw 5 is configured as an engagement hook. The counter snap-in locking member 11 of the joint jaw 6 is configured as an engagement recess which is complementary to the engagement hook 10. The two locking members form a snap-in locking arrangement. In an engagement position of the snap-in locking arrangement 10, 11, which is achieved when the joint jaw 6 is fully folded in relative to the base body jaw 5, the tubing 4 is deformed by at least one jaw deformation component 12, 13 so as to securely accommodate the catheter end section. The jaw deformation components 12, 13 are formed in one piece with a side of the joint jaw 6 facing the base body jaw 5. In addition to the jaw deformation components 12, 13, the joint jaw 6 is also provided with a positioning component 13a to ensure a correct relative positioning of a position of the joint jaw 6 relative to the position of the base body jaw 5 with the tubing 4.

Between the snap-in locking member 10 adjoining the orifice 9 and a head section 14 of the catheter coupling 1 in which the orifice 9 is formed, a groove-like recess 15 is arranged which allows the head section 14 to move relative to the snap-in locking member 10. It is for instance conceivable to move the head section 14 towards the snap-in locking member 10, causing the recess 15 to be slightly narrowed. The head section 14 is able to move relative to the snap-in locking member 10 irrespective of a jaw movement via the jaw joint 7. The groove-like recess 15 extends transversely to the longitudinal axis of the tubing 4, thus forming a semicircular groove about the tubing 4 between the head section 14 and the snap-in locking member 10.

Figure 2:
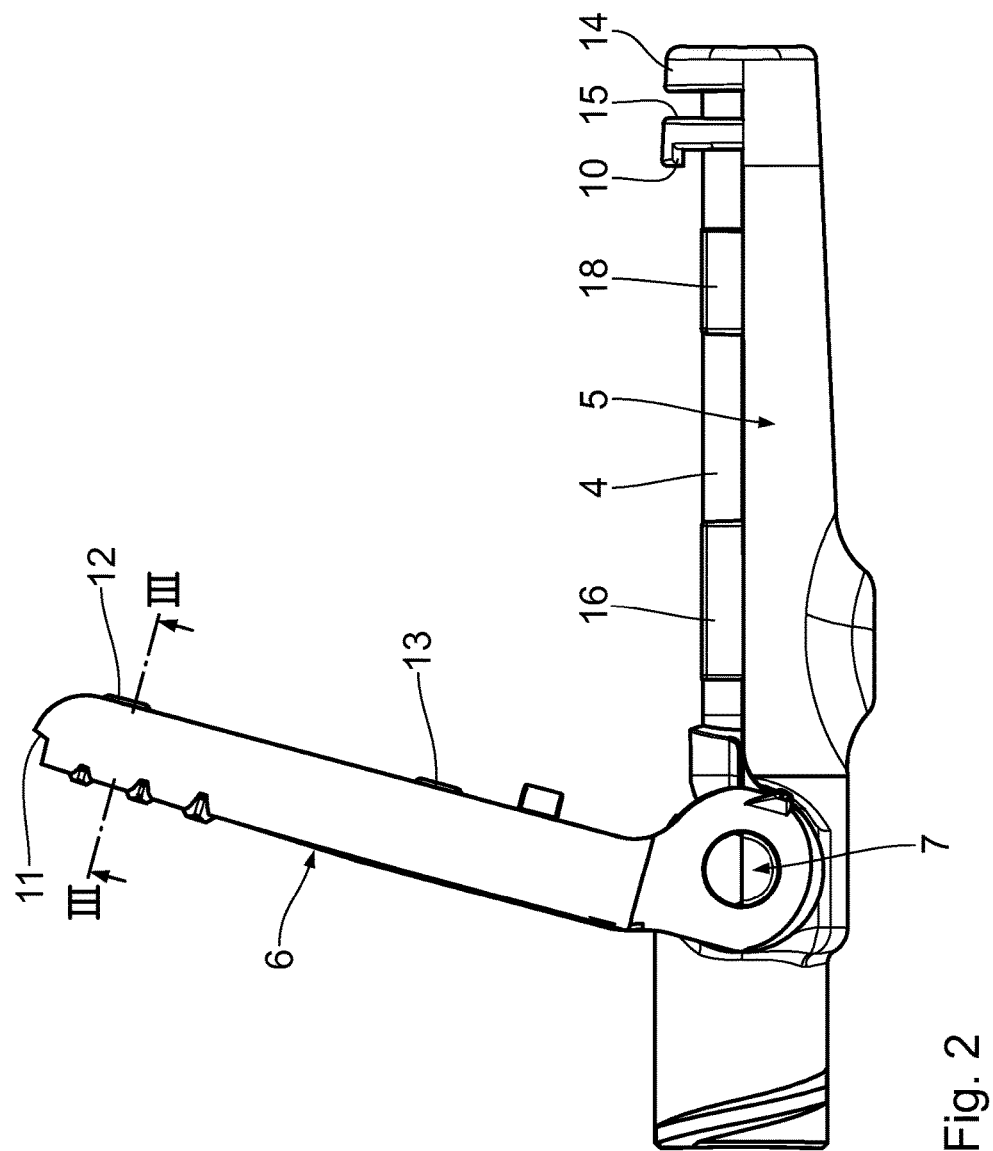
FIG. 2 shows a side view of the catheter coupling with the jaws in a folded-out inclined position according to FIG. 1.

The base body jaw 5 has protective webs 16, 17, 18, 19 between the tubing 4 is arranged in such a way as to be recessed therein as shown in the side view of FIG. 2. When the joint jaw 6 is folded open, the tubing 4 is protected against deformation by the protective webs 16 to 19.

The protective webs 16 to 19 extend in each case along the tubing 4. The protective webs 16 to 19 are formed in one piece with the base body jaw 5. The protective webs 16 to 19 are arranged on both sides of the tubing 4. In the embodiment according to FIGS. 1 to 3, a recess, in other words an interruption, is provided between the protective webs 16, 18 and 17, 19 which are in each case arranged adjacent to each other on a respective side of the tubing 4.

The joint jaw 6 is provided with recesses 20, 21 which are engaged by the protective webs 16 to 19 when the jaws 5, 6 abut against each other. The recesses 20, 21 are substantially complementary to the webs 16 to 19, allowing them to guide a movement of the jaws 5, 6 towards each other in order to reach a protection position of the jaws 5, 6 in which the locking members 10, 11 are in locking engagement and the jaws 5, 6 abut against each other.

Figure 3:
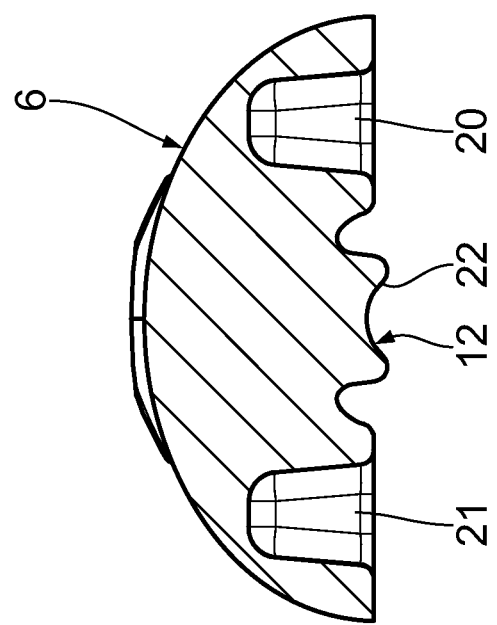
FIG. 3 shows an enlarged cross-sectional view through a joint jaw along line III-III in FIG. 2.

Each of the jaw deformation components, with the jaw deformation component 12 being shown in an enlarged cross-sectional view in FIG. 3, has a concave contact surface 22 which abuts against the outside of the tubing 4 in order to deform the tubing 4 when the jaws 5, 6 abut against each other. The concave contact surfaces 22 of the jaw deformation components 12, 13 are in each case curved about an axis which is parallel to the longitudinal axis of the tubing 4.

The two jaw deformation components 12, 13 are spaced from each other. The jaw deformation component 12 is arranged adjacent to the counter snap-in locking member 11 when seen in the longitudinal direction of the joint jaw 6. The other jaw deformation component 13 is arranged between the jaw deformation component 12 and the joint jaw 7.

The entire catheter coupling 1 is made of plastics.

The catheter coupling 1 is used as follows:

Initially, the catheter coupling 1 is in an open position according to FIGS. 1 and 2. In this open position, the catheter 3 may be inserted through the orifice 9 into the tubing 4 until it reaches a defined stop. Said stop is adjacent to the elevation of the jaw joint 7.

Figure 4:
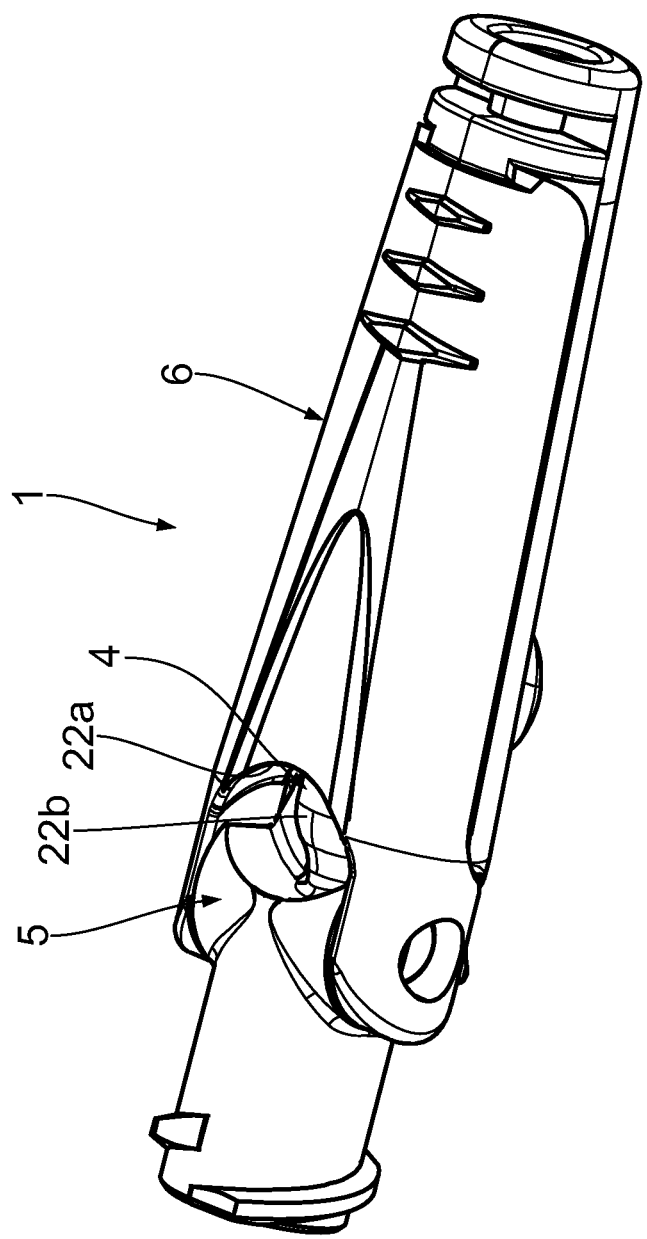
FIG. 4 shows a perspective view of the catheter coupling with the jaws in a folded-in closed position.

In the base body jaw 5, a transparent section, in other words an inspection window 22a, may be arranged in the region of the stop for the end section of the catheter 3. Said transparent section allows a visual inspection to be performed to ensure that the end section of the catheter 3 has reached the stop. FIG. 4 shows the catheter coupling 1 with its jaws 5, 6 closed, wherein the inspection window 22a formed between the joint jaw 6 on the one hand and the base body jaw 5 on the other is visible. At least a section 22b of the tubing 4 is at least partly transparent, thus allowing a position of the end section of the catheter 3 to be visually inspected in section 22b of the tubing 4 via the inspection window 22a.

After the catheter 3 has been fully inserted into the tubing 4 up to the stop, the joint jaw 6 is pivoted about the jaw joint 7 until the snap-in locking members 10, 11 come into locking engagement, thus causing the protective webs 16 to 19 to engage into the recesses 20, 21. When the jaws 5, 6 are locked, the jaw deformation components 12, 13 deform those regions of the tubing 4 abutting against the jaw deformation components 12, 13. This deformation of said regions of the tubing 4 causes the catheter 3 to be secured in the tubing 4 by frictional engagement; the catheter 3 is thus securely connected to the catheter coupling 1. Via a Luer Lock connector not shown in FIGS. 1 to 3, the catheter coupling 1 is connectable to the tube 2 in order to administer for instance a drug, in particular an anaesthetic for epidural anaesthesia.

Figure 5:
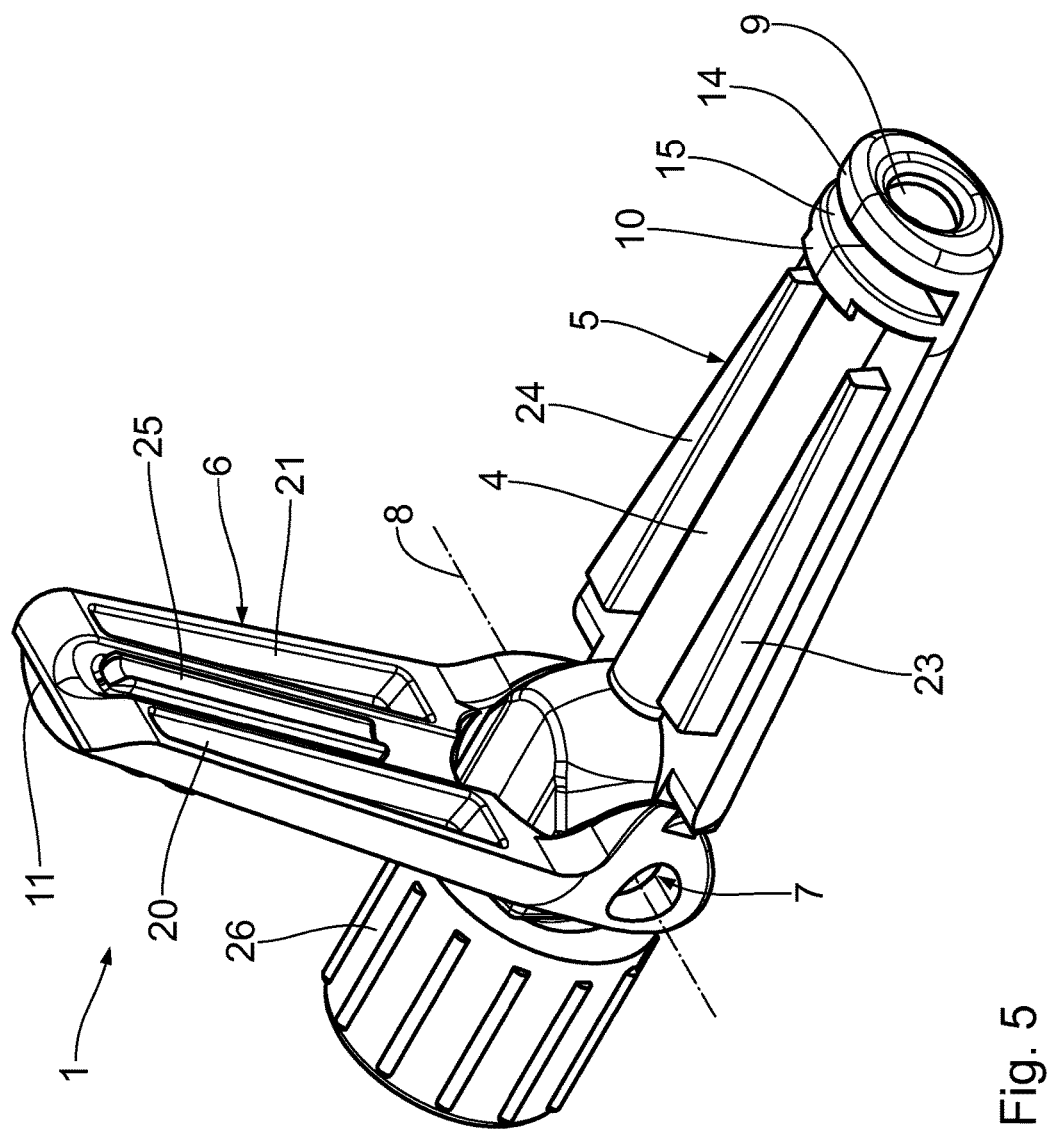
FIG. 5 shows a perspective view from a direction similar to FIG. 1 of another embodiment of a catheter coupling with its jaws folded out as well.

FIG. 5 shows a view of another embodiment of the catheter coupling 1 which is similar to that of FIG. 1. Components and functions which correspond to those already described above with reference to FIGS. 1 to 4 are designated by the same reference numerals and are not discussed in detail again.

Instead of the protective webs 16, 17 and 18, 19, the catheter 1 according to FIG. 5 has two continuous protective webs 23, 24 the function of which corresponds to that of the protective webs 16 to 19.

The catheter 1 according to FIG. 5 further has one single jaw deformation component 25 which extends along approximately two thirds of the jaw joint 6 and has the same cross-section as the jaw deformation components 12, 13 according to FIGS. 1 to 4. Therefore, the jaw deformation component 25 exerts a force on the tubing 4 along its entire length as soon as the jaws 5, 6 abut against each other and are in locking engagement.

The catheter coupling 1 according to FIG. 5 is additionally shown to include a Luer Lock connector 26.

The invention claimed is:

1. A catheter coupling comprising: a tubing and two jaws, namely a base body jaw and a joint jaw, extending in a longitudinal direction of the tubing, wherein the two jaws and the tubing form a channel having an orifice to accommodate an end section of a catheter when the two jaws abut against each other,
   wherein the two jaws are interconnected at a first respective jaw end via a jaw joint having a joint axis extending transversely to the tubing, with a second respective jaw end of the base body jaw having a snap-in locking member, with a second respective jaw end of the joint jaw having a counter snap-in locking member, wherein the snap-in locking member and the counter snap-in locking member interact with one another, causing the two locking members to form a snap-in locking arrangement;
   wherein the tubing is deformed by at least one jaw deformation component to securely accommodate the catheter end section when the snap-in locking arrangement is in an engagement position,
wherein at least one inspection window is formed between the joint jaw and the base body jaw which allows a visual inspection of a stop in the tubing for the end section of the catheter;
   wherein at least a section of the tubing is at least partly transparent,
   wherein a recess is arranged between the snap-in locking member adjacent to the orifice and a head section of the catheter coupling in which the orifice is formed, and
   wherein the recess allows the head section to move relative to the snap-in locking member irrespective of a movement of the joint jaw relative to the base body jaw via the jaw joint.

2. The catheter coupling according to claim 1, wherein the base body jaw is part of a base body of the catheter coupling which carries the tubing, wherein the base body jaw is provided with protective webs between which the tubing is arranged in such a way as to be recessed therein so that the tubing is protected against deformation by the protective webs when the joint jaw is folded open.

3. The catheter coupling according to claim 2, wherein the protective webs comprise continuous protective webs between which the tubing is arranged in such a way as to be recessed therein.

4. The catheter coupling according to claim 2, wherein the joint jaw, which is articulated to the base body jaw, is provided with recesses which are engaged by the protective webs when the two jaws abut against each other.

5. The catheter coupling according to claim 1, wherein the base body jaw is part of a base body of the catheter coupling which carries the tubing.

6. The catheter coupling according to claim 5, wherein the tubing is integrally manufactured with the base body jaw by two-component injection molding, wherein the tubing is configured as a soft component while the base body jaw is configured as a hard component of a two-component configuration.

7. The catheter coupling according to claim 1, wherein the at least one jaw deformation component has a concave contact surface which abuts against the outside of the tubing when the two jaws abut against each other.

8. The catheter coupling according to claim 1, comprising at least two jaw deformation components which are spaced from each other along the tubing when the two jaws abut against each other.

9. The catheter coupling according to claim 1, wherein the two jaws are formed of a substantially hard material and the tubing is formed of a material softer than the two jaws, and wherein the tubing is captured between the two jaws when the two jaws are closed.

10. The catheter coupling according to claim 9, wherein the tubing is deformed when the two jaws are closed.

11. The catheter coupling according to claim 10, wherein the tubing is carried by the base body jaw and deformed by the joint jaw when the base body jaw is closed against the joint jaw.

12. The catheter coupling according to claim 11, wherein the tubing and the base body jaw are formed as a unit.

13. The catheter coupling according to claim 12, wherein the tubing and the base body jaw are formed as a two-component injection-molded unit.

14. The catheter coupling according to claim 1, wherein the tubing is elongate, generally cylindrical and deformed when one of the two jaws is brought into engagement with the other one of the two jaws.

15. The catheter coupling according to claim 14, wherein the tubing is carried by the base body jaw.

16. The catheter coupling according to claim 15, wherein the tubing is deformed by the joint jaw when the two jaws engage one another.

17. The catheter coupling according to claim 1, wherein one of the two jaws has a pair of longitudinally extending webs spaced apart by the tubing longitudinally extending therebetween protecting the tubing and guiding the other one of the two jaws into pivoting engagement with the one of the two jaws, thereby deforming the tubing.

* * * * *